(12) United States Patent
Fu et al.

(10) Patent No.: US 8,663,124 B2
(45) Date of Patent: *Mar. 4, 2014

(54) MULTISTAGE METHOD AND SYSTEM FOR ESTIMATING RESPIRATION PARAMETERS FROM ACOUSTIC SIGNAL

(75) Inventors: Yongji Fu, Vancouver, WA (US); Yungkai Kyle Lai, Aliso Viejo, CA (US); Bryan Severt Hallberg, Vancouver, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 358 days.

This patent is subject to a terminal disclaimer.

(21) Appl. No.: 13/065,815

(22) Filed: Mar. 30, 2011

(65) Prior Publication Data

US 2012/0253214 A1 Oct. 4, 2012

(51) Int. Cl.
 *A61B 5/08* (2006.01)
(52) U.S. Cl.
 USPC .......................................................... 600/529
(58) Field of Classification Search
 USPC ................................................ 600/529–543
 See application file for complete search history.

(56) References Cited

U.S. PATENT DOCUMENTS

| | | | | |
|---|---|---|---|---|
| 4,306,567 A | * | 12/1981 | Krasner | 600/484 |
| 5,143,078 A | * | 9/1992 | Mather et al. | 600/529 |
| 6,654,623 B1 | * | 11/2003 | Kastle | 600/336 |
| 7,174,206 B2 | | 2/2007 | Frei et al. | |
| 7,267,652 B2 | | 9/2007 | Coyle et al. | 600/538 |
| 7,404,802 B2 | | 7/2008 | Siejko et al. | 600/528 |
| 7,412,281 B2 | | 8/2008 | Shen et al. | |
| 7,460,901 B2 | | 12/2008 | Kettunen | 600/513 |
| 7,502,643 B2 | | 3/2009 | Farringdon et al. | 600/509 |
| 7,515,044 B2 | | 4/2009 | Welch et al. | 340/539.12 |
| 7,515,054 B2 | | 4/2009 | Torch | 340/573.1 |
| 7,761,128 B2 | | 7/2010 | Al-Ali et al. | |
| 7,762,953 B2 | | 7/2010 | Derchak et al. | |
| 7,813,780 B2 | | 10/2010 | Shah et al. | |
| 7,818,049 B2 | | 10/2010 | Halperin et al. | |
| 2005/0061315 A1 | | 3/2005 | Lee et al. | |
| 2007/0282212 A1 | | 12/2007 | Sierra et al. | |
| 2010/0256505 A1 | | 10/2010 | Xu et al. | |
| 2011/0054339 A1 | * | 3/2011 | Gass et al. | 600/529 |

(Continued)

OTHER PUBLICATIONS

Yongji Fu et al., Pulmonary Disease Management System with Distributed Wearable Sensors, 31st Ann. Int'l Conf. IEEE EMBS, Sep. 6, 2009, pp. 773-776.

(Continued)

*Primary Examiner* — Michael Kahelin
*Assistant Examiner* — Karen Toth
(74) *Attorney, Agent, or Firm* — Scot A. Reader

(57) ABSTRACT

A multistage system and method for estimating respiration parameters from an acoustic signal. At a first stage, the method and system detect and isolate portions of the signal that exhibit long-term, moderate amplitude noise by analyzing cumulative energies in the signal, and portions of the signal that exhibit short-term, high amplitude noise by analyzing peak energies in the signal. At a second stage, the method and system filter heart sound from the signal energy envelope by applying an adaptive filter that minimizes the loss of respiration sound. At a third stage, the system and method isolate respiration phases in the signal by identifying trends in the energy envelope. Once respiration phases are isolated, these phases are used to estimate respiration parameters, such as respiration rate and I/E ratio.

18 Claims, 13 Drawing Sheets

(56) References Cited

U.S. PATENT DOCUMENTS

| | | | |
|---|---|---|---|
| 2011/0295138 A1* | 12/2011 | Lai et al. | 600/529 |
| 2012/0029298 A1* | 2/2012 | Fu et al. | 600/300 |
| 2012/0071744 A1* | 3/2012 | Euliano et al. | 600/382 |
| 2012/0253215 A1* | 10/2012 | Fu et al. | 600/529 |

OTHER PUBLICATIONS

Yongji Fu et al., Signal Quality Classification for an Ambulatory Monitoring System, 32nd Ann. Int'l Conf. IEEE EMBS, Sep. 4, 2010, pp. 174-177.

* cited by examiner

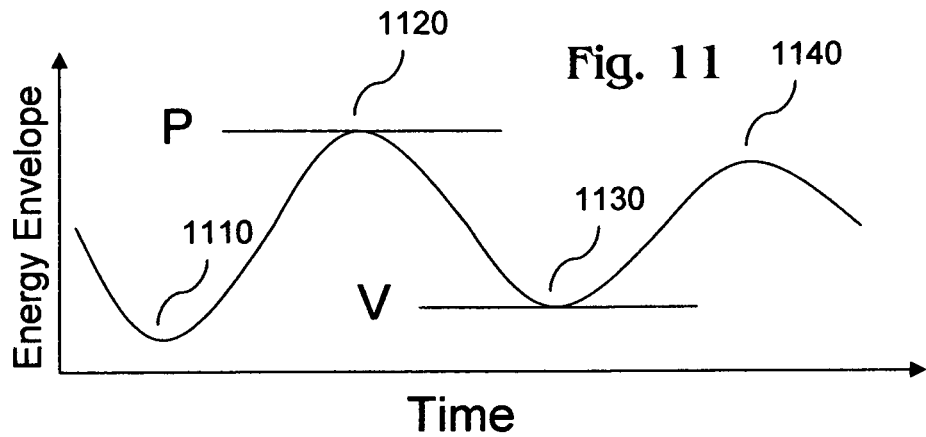
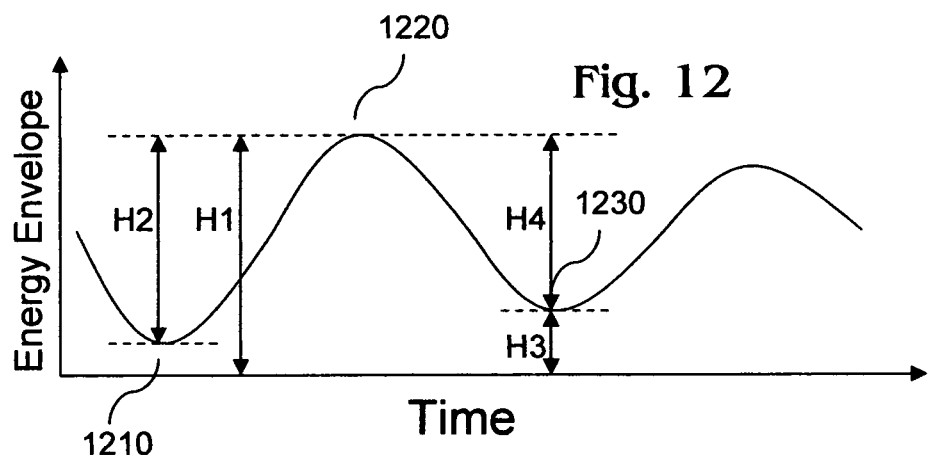
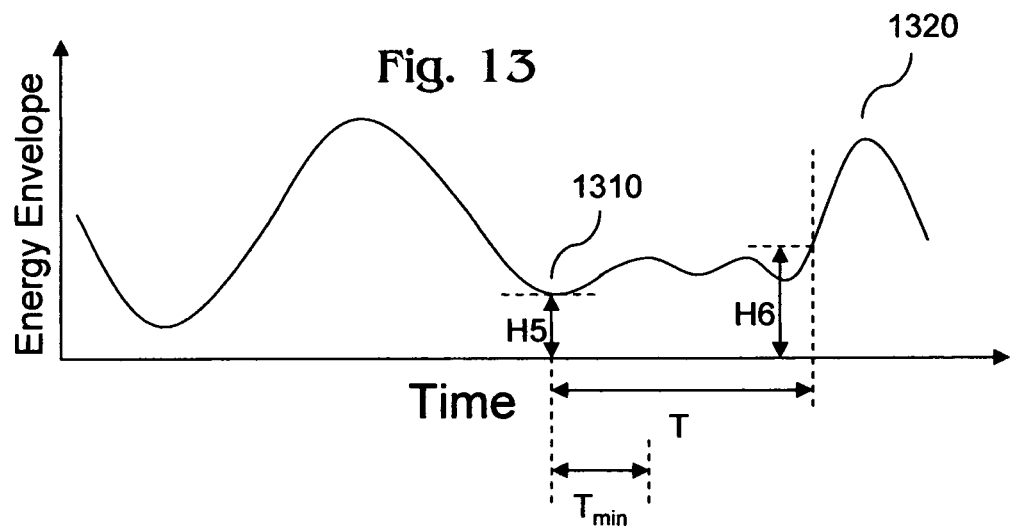

MULTISTAGE METHOD AND SYSTEM FOR ESTIMATING RESPIRATION PARAMETERS FROM ACOUSTIC SIGNAL

CROSS-REFERENCE TO RELATED APPLICATION(S)

This application has subject matter related to application Ser. No. 13/065,816 entitled "DUAL PATH NOISE DETECTION AND ISOLATION FOR ACOUSTIC AMBULATORY RESPIRATION MONITORING SYSTEM," filed Mar. 30, 2011, published as U.S. Patent Application Publication No. 2012/0253215.

BACKGROUND OF THE INVENTION

The present invention relates to physiological monitoring and, more particularly, to acoustic ambulatory respiration monitoring.

Ambulatory respiration monitoring can be helpful in maintaining the respiratory health of people as they go about their daily lives. For example, continuous monitoring of respiration rate using a portable device can enable prompt discovery of a problem with the respiratory health of a person who suffers from a chronic pulmonary disease or works in hazardous environment so that the person can obtain timely treatment. Ambulatory respiration monitoring can also be useful for other purposes, such as senior monitoring and sleep monitoring.

Many different respiration monitoring systems are known. Some of these systems are airflow systems. In these systems, a subject breathes into an apparatus that measures the airflow through his or her mouth and respiration rate is estimated from the airflow. Other systems measure the subject's volume, movement or tissue concentrations. For example, in a respiratory inductance plethysmography (RIP) system, a subject wears a first inductance band around his or her ribcage and a second inductance band around his or her abdomen. As the subject breathes, the volumes of the ribcage and abdominal compartments change, which alter the inductance of coils, and the subject's respiration rate is estimated based on the changes in inductance. Unfortunately, these systems are much better suited for stationary monitoring than ambulatory monitoring.

Other respiration monitoring systems derive a subject's respiration rate from an electrocardiogram (ECG)-based wearable sensor. While these systems can be applied in ambulatory respiration monitoring, ECG-derived respiration rate measurements are highly sensitive to motion and often unreliable in ambulatory contexts.

For these reasons, many ambulatory respiration monitoring systems invoke the respiration sound method, sometimes called auscultation, to estimate a subject's respiration rate. In the respiration sound method, an acoustic transducer mounted on the body of the person being monitored captures and acquires an acoustic signal recording respiration sounds. The sound transducer is typically placed over the suprasternal notch or at the lateral neck near the pharynx because lung sounds captured in that region typically have a high signal-to-noise ratio and a high sensitivity to variation in flow. Once the acoustic signal with recorded respiration sounds has been generated, respiration phases are identified in the acoustic signal and respiration parameter estimates [e.g., respiration rate, inspiration/expiration (I/E) ratio] are calculated. Respiration health status information based on respiration parameter estimates may then be outputted locally to the monitored person or remotely to a clinician.

While ambulatory respiration monitoring systems that invoke the respiration sound method hold considerable promise, numerous obstacles to accurate respiration parameter estimation have arisen in these systems, including noise in the acoustic signal (both long-term background noise and short-term impulse noise), heart sound comingled with respiration sound in the acoustic signal, and variation in human respiration patterns.

SUMMARY OF THE INVENTION

The present invention provides a multistage system and method for estimating respiration parameters from an acoustic signal. At a first stage, the method and system detect and isolate portions of the signal that exhibit long-term, moderate amplitude noise by analyzing cumulative energies in the signal, and portions of the signal that exhibit short-term, high amplitude noise by analyzing peak energies in the signal. At a second stage, the method and system filter heart sound from the signal energy envelope by applying an adaptive filter that minimizes the loss of respiration sound. At a third stage, the system and method isolate respiration phases in the signal by identifying trends in the energy envelope. Once respiration phases are isolated, these phases are used to estimate respiration parameters, such as respiration rate and I/E ratio.

In one aspect of the invention, therefore, a method for processing an acoustic signal comprises the steps of acquiring by a respiration monitoring system an acoustic signal recording body sounds; isolating by the system noisy portions of the signal based at least in part on cumulative energies and peak energies in the signal; detecting by the system an energy envelope for non-noisy portions of the signal; filtering by the system the energy envelope using an adaptive filter; isolating by the system respiration phases in the energy envelope at least in part by identifying trends in the energy envelope; estimating by the system a respiration parameter based at least in part on the respiration phases; and outputting by the system information based at least in part on the respiration parameter estimate.

In some embodiments of the invention, the first isolating step comprises the substeps of detecting first noisy portions of the signal based at least in part on cumulative energies in the signal; detecting second noisy portions of the signal based at least in part on peak energies in the signal; and identifying the isolated noisy portions based at least in part on the first noisy portions and the second noisy portions.

In some embodiments, the identifying substep comprises designating, as third noisy portions, intersections between first noisy portions that envelop second noisy portions and second noisy portions that are enveloped by first noisy portions.

In some embodiments, the identifying substep comprises designating, as third noisy portions, unions of first noisy portions that do not envelop second noisy portions and second noisy portions that are not enveloped by first noisy portions.

In some embodiments, the filtering step comprises the substeps of identifying unwanted peaks in the energy envelope that are attributable to heart sound; decreasing a high cutoff frequency in response to identifying the unwanted peaks; and applying the decreased high cutoff frequency to the energy envelope.

In some embodiments, the filtering step further comprises the subteps of identifying wanted peaks that were removed from the energy envelope in response to applying the decreased high cutoff frequency; and increasing the high cutoff frequency in response to identifying the wanted peaks.

In some embodiments, the second isolating step comprises the substeps of identifying candidate peaks at maxima of the energy envelope; identifying candidate valleys at minima of the energy envelope; selecting significant peaks from among the candidate peaks using heights of the candidate peaks; selecting significant valleys from among the candidate valleys using heights of the candidate valleys; detecting silent phases in the energy envelope based at least in part on rise rates from the significant valleys; and isolating the respiration phases based at least in part on the significant valleys and the silent phases.

In some embodiments, the isolating substep comprises identifying a true silent phase among the silent phases based at least in part on a respiration phase sequence exhibited by the energy envelope.

In some embodiments, the isolating substep comprises identifying a silent expiration phase among the silent phases based at least in part on a respiration phase sequence exhibited by the energy envelope.

In another aspect of the invention, a respiration monitoring system comprises a sound capture system adapted to acquire an acoustic signal recording body sounds; an acoustic signal processing system adapted to receive from the sound capture system the signal, isolate noisy portions of the signal based at least in part on cumulative energies and peak energies in the signal, detect an energy envelope for non-noisy portions of the signal, filter the energy envelope using an adaptive filter, isolate respiration phases in the energy envelope at least in part by identifying trends in the energy envelope and estimate a respiration parameter based at least in part on the respiration phases; and a respiration data output system adapted to output information based at least in part on the respiration parameter estimate.

In some embodiments, the respiratory monitoring system is a portable ambulatory monitoring device.

These and other aspects of the invention will be better understood by reference to the following detailed description taken in conjunction with the drawings that are briefly described below. Of course, the invention is defined by the appended claims.

BRIEF DESCRIPTION OF THE DRAWINGS

FIG. 11 shows use of signal maxima and minima to identify a candidate peak and valley in a signal energy envelope in some embodiments of the invention.

FIG. 12 shows use of signal heights to select a significant peak and valley in a signal energy envelope in some embodiments of the invention.

FIG. 13 shows use of a signal rise rate to identify a silent phase in a signal energy envelope in some embodiments of the invention.

DETAILED DESCRIPTION OF A PREFERRED EMBODIMENT

Figure 1:
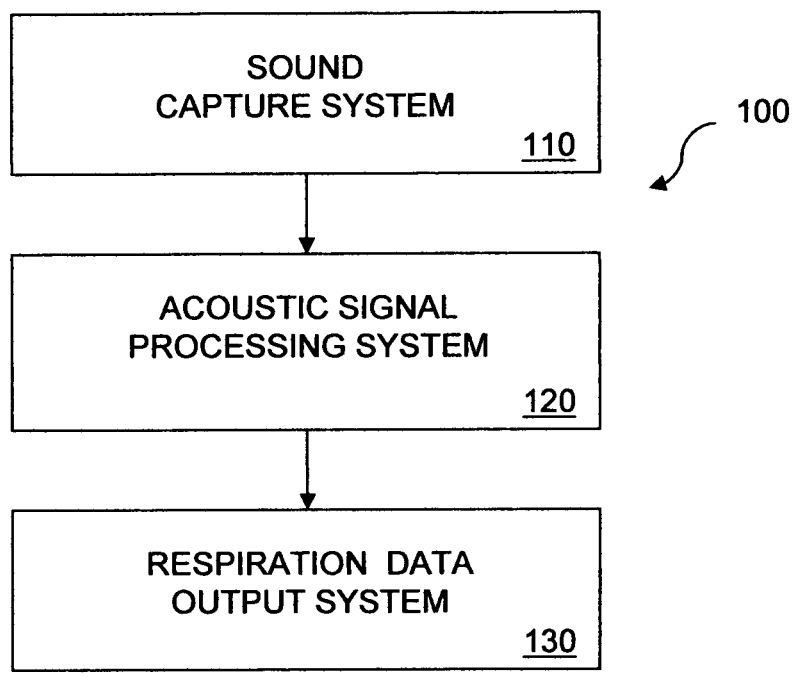
FIG. 1 shows a respiration monitoring system in some embodiments of the invention.

In FIG. 1, a respiration monitoring system 100 is shown in some embodiments of the invention. Monitoring system 100 includes a sound capture system 110, an acoustic signal processing system 120 and a respiration data output system 130 communicatively coupled in series. Monitoring system 110 continually acquires and processes an acoustic signal recording body sounds and continually outputs respiration parameter estimates based on the acoustic signal. In some embodiments, monitoring system 100 is a portable ambulatory monitoring device that monitors a human subject's respiratory health in real-time as the person performs daily activities or in other contexts, such as senior monitoring or sleep monitoring. In other embodiments, capture system 110, processing system 120 and output system 130 may be part of separate devices that are remotely coupled via wired or wireless data communication links.

Capture system 110 continually detects body sounds, including respiration and heart sounds, at a detection point, such as a trachea, chest or back of a person being monitored, and continually transmits an acoustic signal recording the detected body sounds to processing system 120. Capture system 110 may include, for example, a sound transducer positioned on the body of a human subject that detects body sounds, as well as amplifiers, filters, an analog/digital converter and/or automatic gain control that generate an acoustic signal embodying the detected body sounds.

Processing system 120, under control of one or more processors executing software instructions, continually processes the acoustic signal received from capture system 110 and generates and outputs to output system 130 estimates of one or more respiration parameters for the monitored subject. Monitored respiration parameters may include, for example, respiration rate, fractional inspiration time and/or I/E ratio. Processing system 120 performs a multistaged processing on the acoustic signal received from capture system 110. At a first stage, processing system 120 detects and isolates portions of the signal that exhibit long-term, moderate amplitude noise by analyzing cumulative energies in the signal, and also detects and isolates portions of the signal that exhibit short-term, high amplitude noise by analyzing peak energies in the signal. At a second stage, processing system 120 filters heart sound from the signal energy envelope by applying an adaptive filter that minimizes the loss of respiration sound. At a third stage, processing system 120 isolates respiration phases in the energy envelope by identifying trends in the energy envelope. Once respiration phases are isolated, processing system 120 uses them to estimate respiration parameters, such as respiration rate and I/E ratio, and outputs the respiration parameter estimates to output system 130. In other embodiments, processing system 120 may perform processing operations described herein in custom logic, or in a combination of software and custom logic.

In some embodiments, output system 130 has a display screen for displaying respiration data determined using respiration parameter estimates received from processing system 120. In some embodiments, output system 130 in lieu of or in addition to a display screen has an interface to an internal or external data management system that stores respiration data determined using respiration parameter estimates received from processing system 120 and/or an interface that transmits respiration data determined using respiration parameter estimates received from processing system 120 to a remote monitoring device, such as a monitoring device at a clinician facility. Respiration data outputted by output system 130 may include respiration parameter estimates received from processing system 120 and/or respiration data derived from such respiration parameter estimates.

Figure 2:
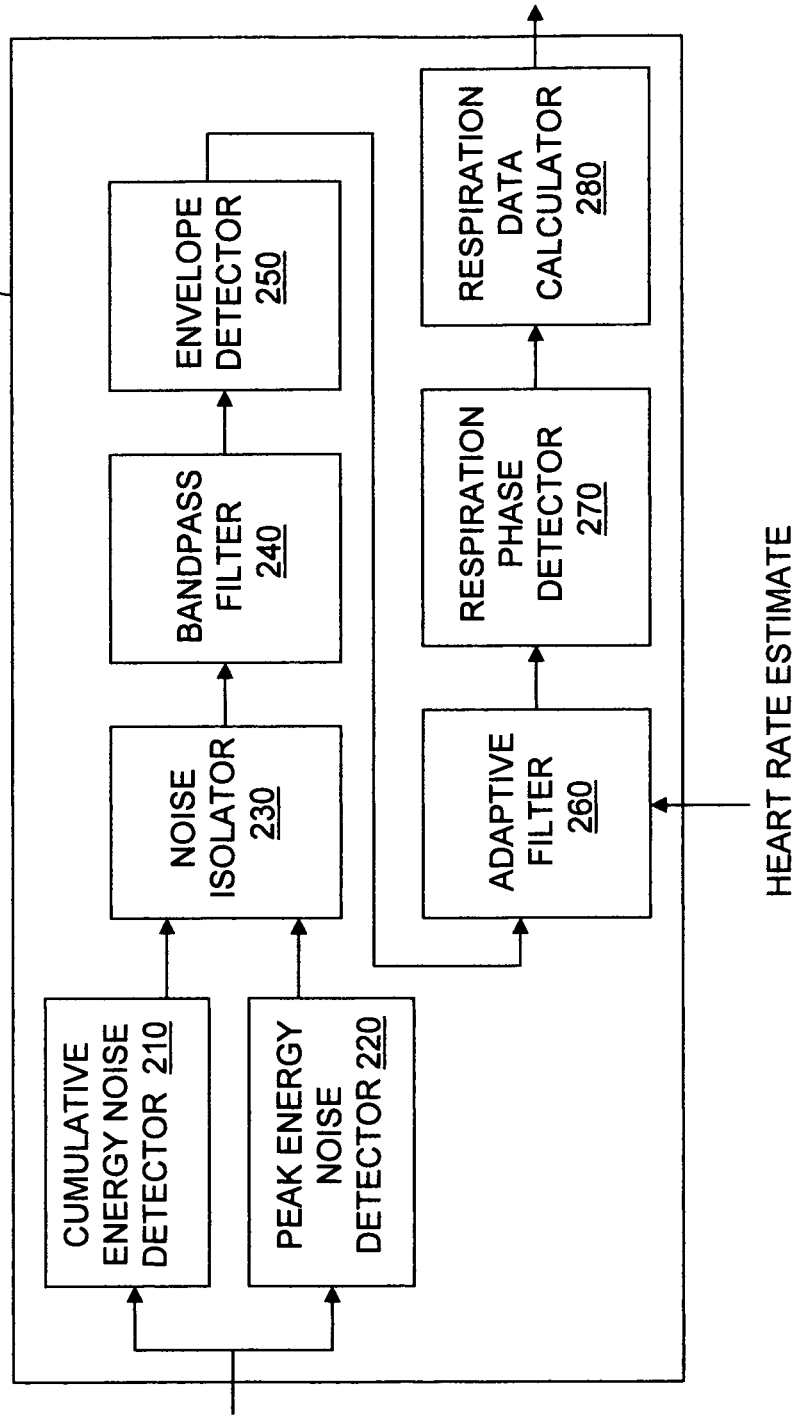
FIG. 2 shows an acoustic signal processing system in some embodiments of the invention.

FIG. 2 shows processing system 120 to include a cumulative energy (CE) noise detector 210 and a peak energy (PE) noise detector 220 operating on separate paths, followed in sequence by a noise isolator 230. As described in FIGS. 3-5 in some embodiments, detectors 210, 220 and isolator 230, under processor control, combine to deliver a dual path noise detection and isolation capability that operates on a raw acoustic signal continually received from capture system 110 to detect and isolate noisy portions of the signal.

Figure 3:
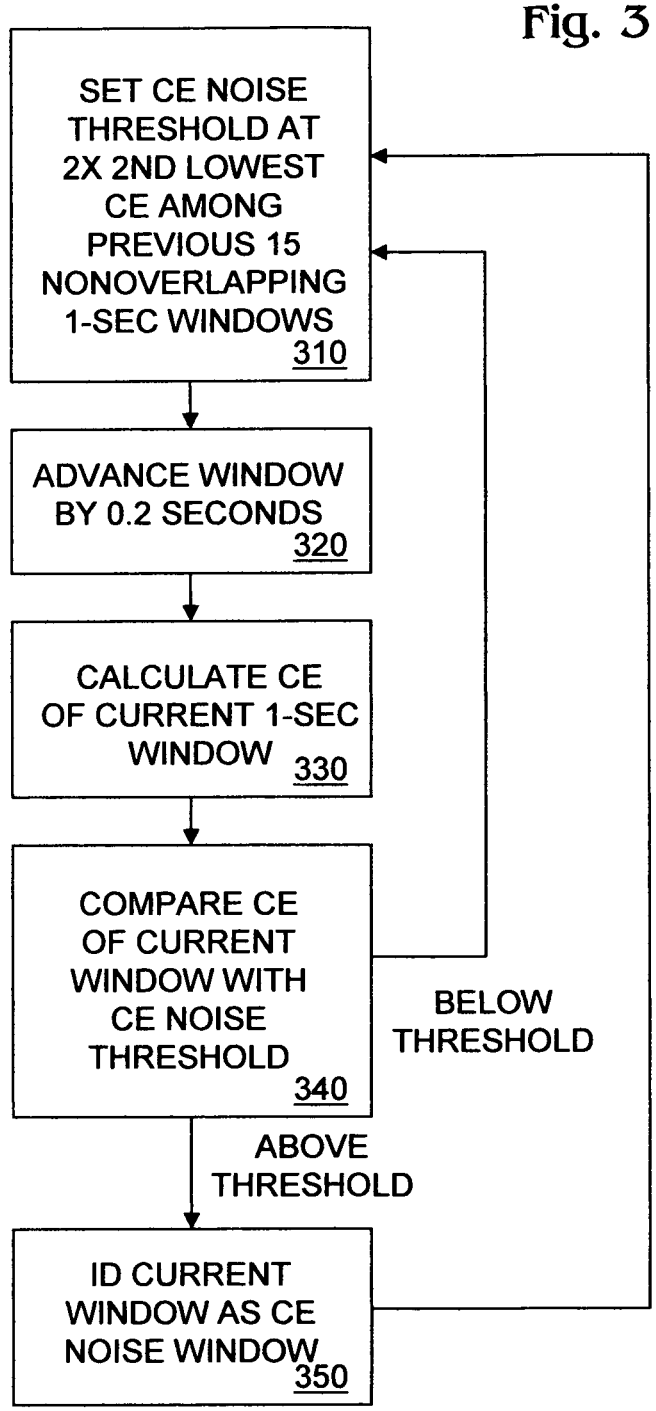
FIG. 3 shows acoustic signal processing steps performed by a cumulative energy noise detector in some embodiments of the invention.
Figure 6A:
FIG. 6A shows the absolute value of a first exemplary acoustic signal segment.
Figure 6B:
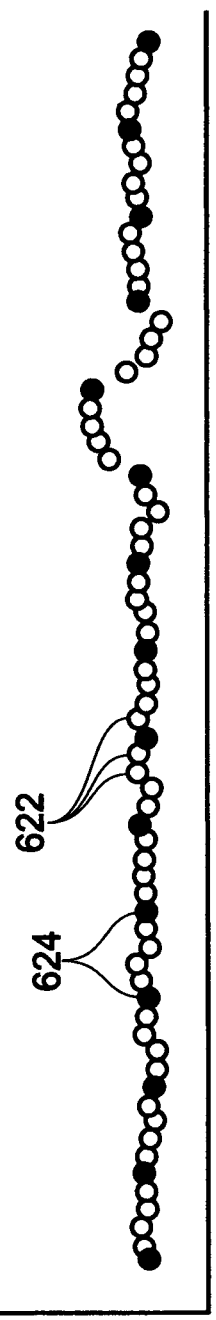
FIG. 6B shows cumulative energy data generated from the first segment.

In runtime operation, a raw acoustic signal is continually fed to a CE noise detector 210 and a PE noise detector 220 and subjected in parallel to the following steps. Turning first to FIG. 3, at CE noise detector 210, a dynamic CE noise threshold for application to a current one-second window is set at two times the second lowest calculated CE among the fifteen immediately preceding non-overlapping one-second windows (310). Default CEs are used until fifteen windows become available. The current window, which is a sliding window, is then advanced by 0.2 seconds (320). The CE of the current window is then calculated by summing the square of the signal over the current window (325). The CE of the current window is then compared with the CE noise threshold (330). If the CE of the current window is above the CE noise threshold, the current window is identified as a CE noise window (350) and the flow returns to Step 310 where the CE noise threshold is updated and applied to the next window (offset 0.2 seconds from the current window). If, however, the CE of the current window is below the CE noise threshold, the flow returns to Step 310 without identifying the current window as a CE noise window. For example, FIG. 6A shows the absolute value of a first exemplary raw acoustic signal segment received by CE noise detector 210. FIG. 6B shows cumulative energy data generated from the first segment after processing by CE noise detector 210. Each white dot (e.g., 622) represents a CE of a current window calculated by summing the square of the signal over the current window. Each black dot (e.g., 624) represents one of the fifteen non-overlapping CEs used to calculate the CE noise threshold.

Figure 4:
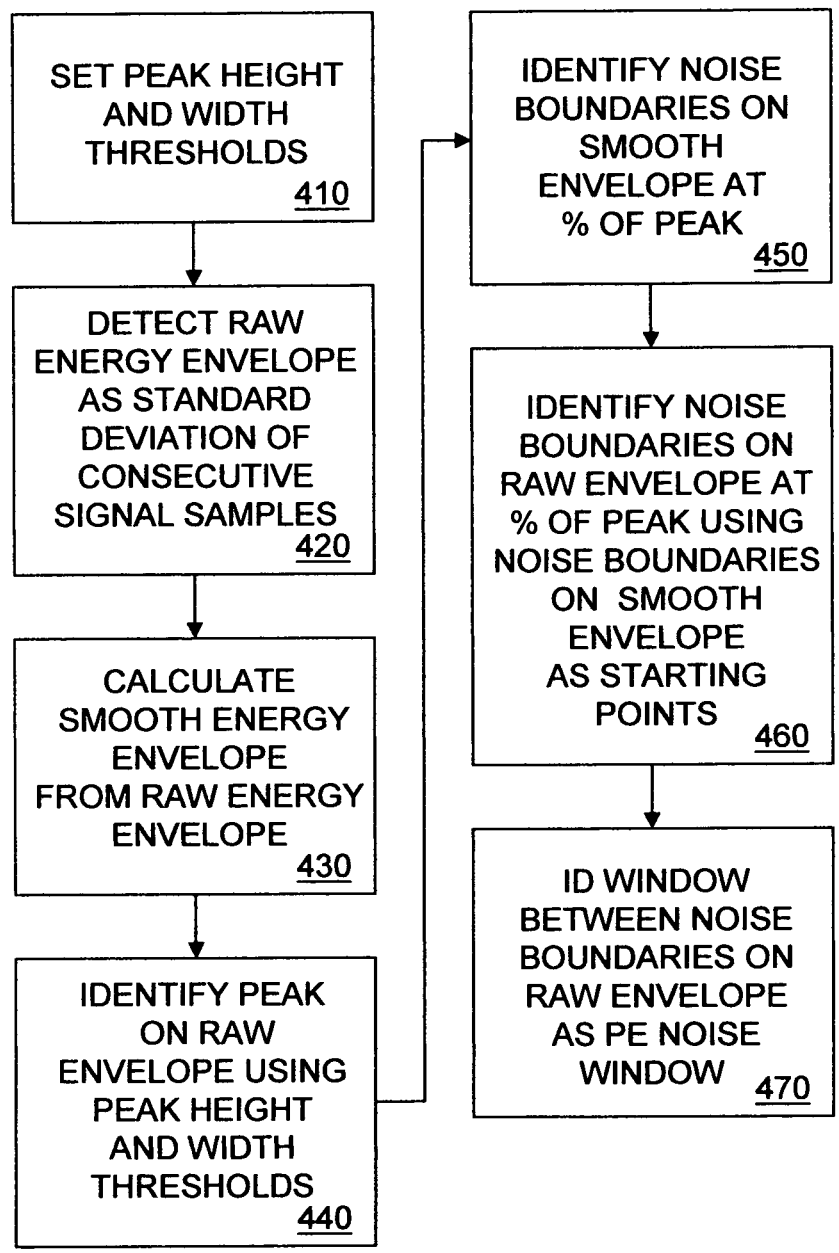
FIG. 4 shows acoustic signal processing steps performed by a peak energy noise detector in some embodiments of the invention.
Figure 5:
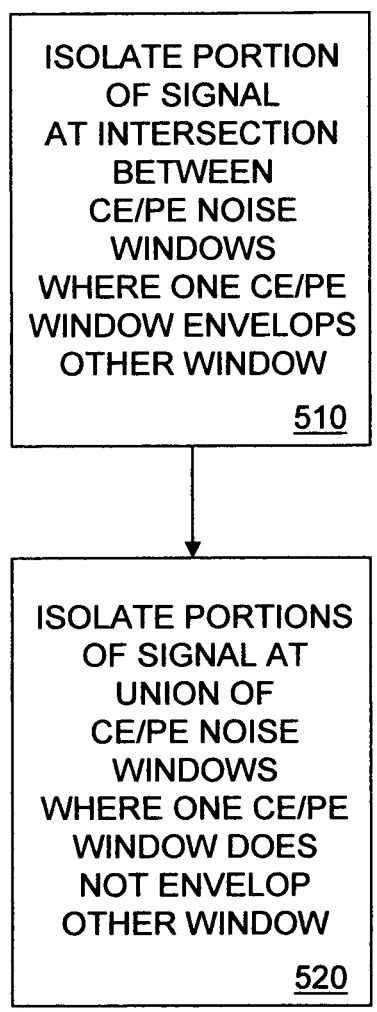
FIG. 5 shows acoustic signal processing steps performed by a noise isolator in some embodiments of the invention.
Figure 6C:
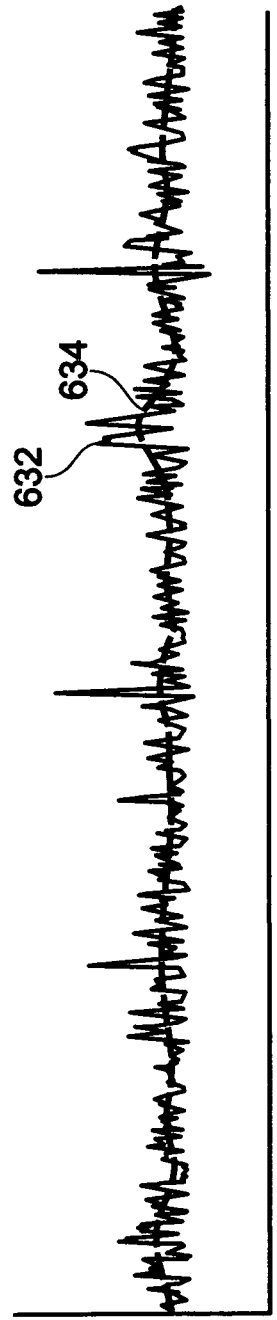
FIG. 6C shows signal energy envelopes detected from the first segment.

FIG. 4 shows runtime operation at PE noise detector 220. Before runtime operation, peak height and width thresholds are configured (410). When the raw acoustic signal is received, the standard deviation of a certain number of (e.g., 20) consecutive samples of the signal is calculated to detect a raw energy envelope (420). A smooth energy envelope is then generated by applying a smoothing function to the raw energy envelope (430). Peaks that exceed the peak height and width thresholds are then identified on the raw energy envelope (440). Left and right noise boundaries for each peak are then identified as follows: First, as the raw energy envelope may exhibit large fluctuation, preliminary noise boundaries are identified along the smooth energy envelope on the left and right side of the peak at a first percentage of the peak amplitude (450). Final noise boundaries are then identified along the raw energy envelope on the left and right side of the peak by tracing upward along the raw energy envelope starting from the left and right preliminary noise boundaries until a second percentage of the peak amplitude is reached (460). The first and second percentages used in noise boundary identification are configured prior to runtime operation. Finally, the window between the noise boundaries on the raw energy envelope is marked as a PE noise window (470). FIG. 6C shows energy envelopes detected from the first segment after processing by PE noise detector 220. The energy envelopes include a raw energy envelope 632 and smooth energy envelope 634.

After processing by CE noise detector 210 and PE noise detector 220, the raw acoustic signal with detected CE and PE noise windows is fed to a noise isolator 230. Noise isolator 230 designates as final noise windows and isolates the intersection of portions of the signal where a CE noise window envelops a PE noise window and the intersection of portions of the signal where a PE noise window envelops a CE noise window (510). Noise isolator 230 also designates as final windows and isolates the union of portions of the signal where a CE noise window is found that does not envelop a PE noise window and portions of the signal where a PE noise window is found that does not envelop a CE noise window (520).

Figure 7A:
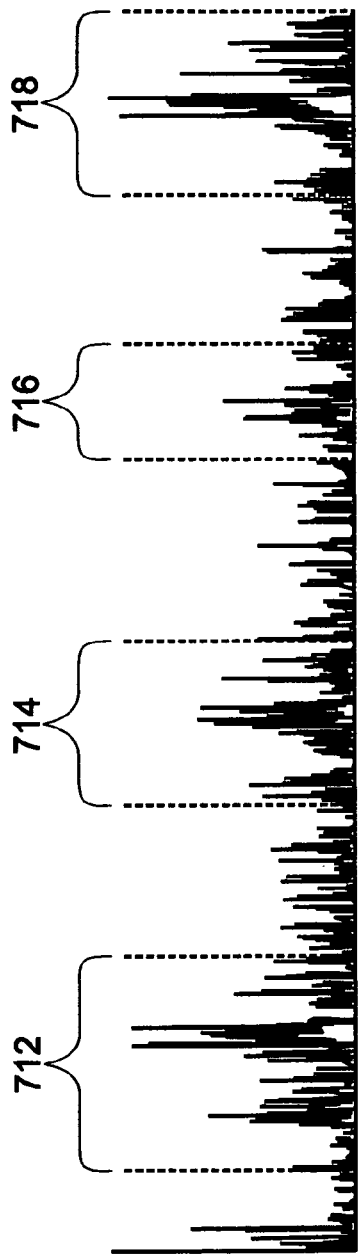
FIG. 7A shows the absolute value of a second exemplary acoustic signal segment, with detected cumulative energy noise windows.
Figure 7B:
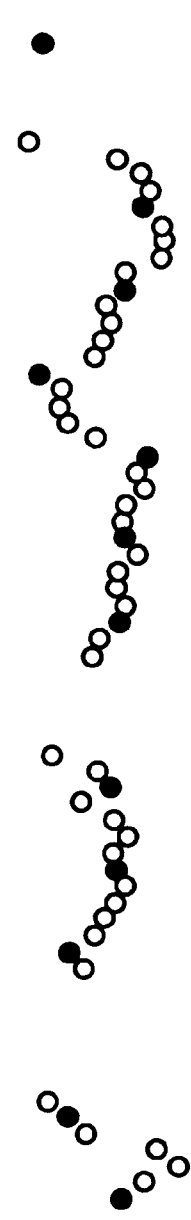
FIG. 7B shows cumulative energy data generated from the second segment.
Figure 7C:
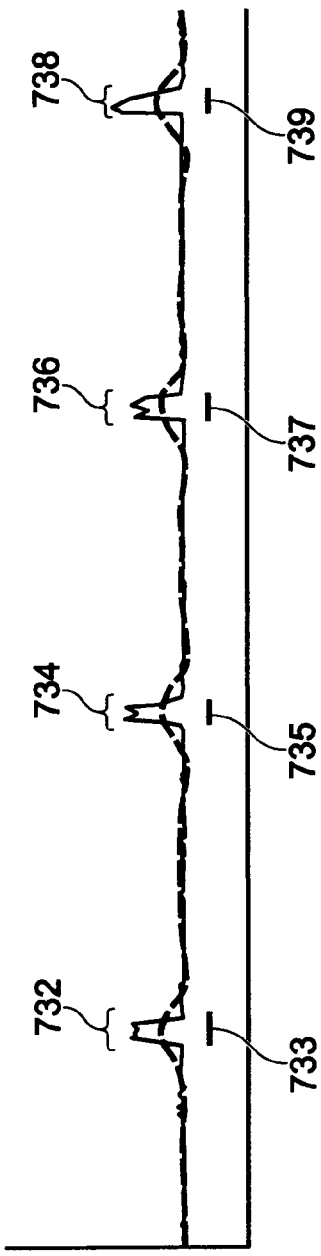
FIG. 7C shows signal energy envelopes detected from the second segment, with detected peak energy noise windows and isolated portions of the segment.

FIGS. 7A-7C illustrate processing of a second exemplary acoustic signal segment by detectors 210, 220 and isolator 230. FIG. 7A shows the absolute value of the raw segment as received by CE noise detector 210 and PE noise detector 220. FIG. 7B shows cumulative energy data generated from the segment after processing by CE noise detector 210. CE noise windows 712, 714, 716, 718 detected as a result of such processing are identified in FIG. 7A. FIG. 7C shows energy envelopes detected from the segment after processing by PE noise detector 220. PE noise windows 732, 734, 736, 738 detected as a result of such processing are identified in FIG. 7C. Since CE noise windows 712, 714, 716, 718 envelop PE noise windows 732, 734, 736, 738, respectively, noise isolator 230 designates as final noise windows 733, 735, 737, 739 the intersection between CE noise windows 712, 714, 716, 718 and PE noise windows 732, 734, 736, 738 and isolates final noise windows 732, 734, 736, 738.

Figure 8A:
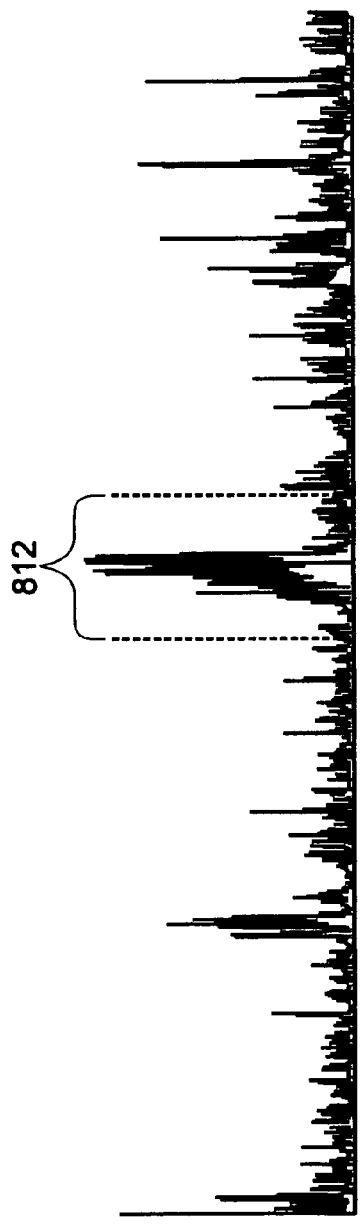
FIG. 8A shows the absolute value of a third exemplary acoustic signal segment, with detected cumulative energy noise windows.
Figure 8B:
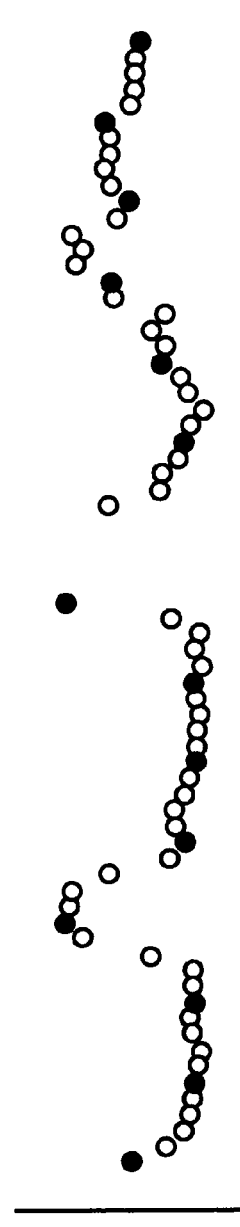
FIG. 8B shows cumulative energy data generated from the third segment.
Figure 8C:
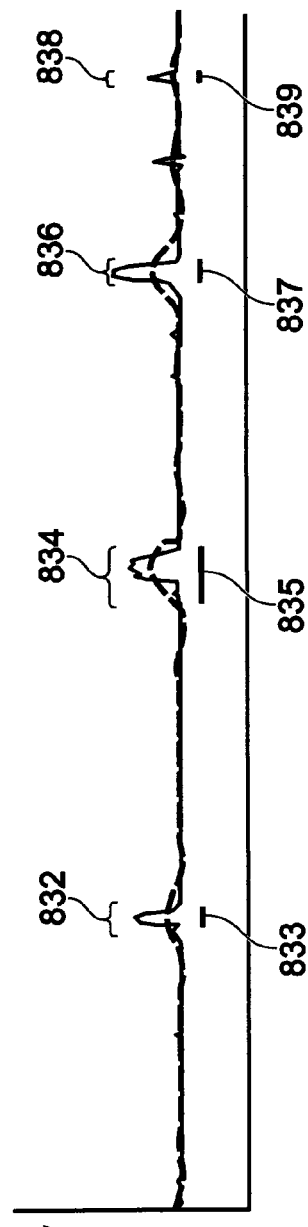
FIG. 8C shows signal energy envelopes detected from the third segment, with detected peak energy noise windows and isolated portions of the segment.

FIGS. 8A-8C illustrate processing of a third exemplary acoustic signal segment by detectors 210, 220 and isolator 230. FIG. 7A shows the absolute value of the raw segment as received by CE noise detector 210 and PE noise detector 220. FIG. 7B shows cumulative energy data generated from the segment after processing by CE noise detector 210. CE noise window 812 is detected as a result of such processing and identified in FIG. 8A. FIG. 8C shows energy envelopes detected from the segment after processing by PE noise detector 220. PE noise windows 832, 834, 836, 838 detected as a result of such processing are identified in FIG. 8C. Since CE noise window 812 envelops PE noise window 834, noise isolator 230 designates as a final noise window 835 the intersection between CE noise window 812 and PE noise window 834. However, since other PE noise windows 832, 836, 838 are not enveloped by any CE noise window and do not envelop any CE noise window, noise isolator 230 designates the union of these windows 832, 836, 838 as final noise windows 833, 837, 839. Noise isolator 230 isolates final noise windows 833, 835, 837, 839.

Next, a band-pass filter 240 receives the raw acoustic signal along with the designated final noise windows. Band-pass filter 240 applies a high-pass cutoff frequency and a low-pass cutoff frequency to the non-noisy portions of the signal to remove components that are obviously not related to respiration sound. In other embodiments, a low-pass filter may be applied instead of a band-pass filter. In still other embodiments, the signal may be passed directly from noise isolator 230 to envelope detector 250 without application of any band-pass or low-pass filter.

Next, an envelope detector 250 detects a signal energy envelope for the non-noisy portions of the signal. In some embodiments, envelope detector 250 also has a smoothing module that applies to the detected energy envelope a smooth finite impulse response filter.

Next, an adaptive filter 260 is applied to the energy envelope to remove additional relatively fast-changing non-respiration sounds (e.g., heart sound) while minimizing the loss of respiration sound. Adaptive filter 260 applies an adaptive cutoff frequency and after one or more iterations finds an optimized cutoff frequency that strikes an appropriate balance between removal of non-respiration sounds and retention of respiration sound for the particular human subject being monitored.

Figure 9:
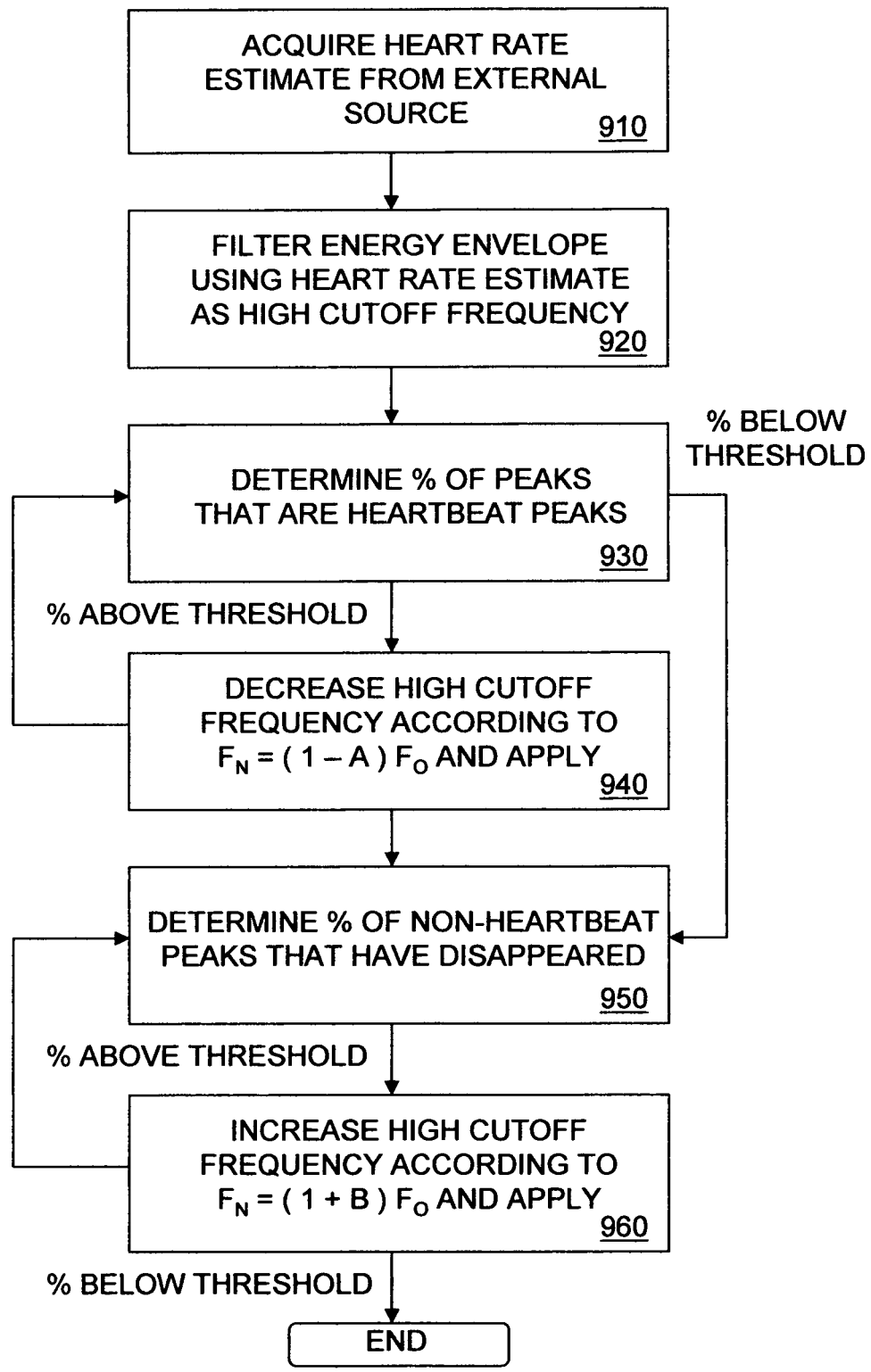
FIG. 9 shows signal energy envelope processing steps performed by an adaptive filter in some embodiments of the invention.

FIG. 9, shows energy envelope processing steps performed by adaptive filter 260 in some embodiments of the invention. Adaptive filter 260 acquires a heart rate estimate the subject being monitored from an external source (910). Adaptive filter 260 then filters the energy envelope using the heart rate estimate as a high bound cutoff frequency (920). Adaptive filter 260 then determines a percentage of peaks in the energy envelope that are unwanted peaks attributable to heart sound (930). In this regard, adaptive filter 260 analyzes consecutive peaks and identifies as "heartbeat" peaks consecutive peaks whose separation in time is close to (i.e., within a predetermined time threshold) the heart rate estimate. If the percentage of these "heartbeat" peaks relative to total peaks is above a threshold percentage, it is presumed that heart sound has not been adequately filtered and adaptive filter 260 decreases the high bound cutoff frequency according to the formula $$F_N = (1-A)F_O$$

where $F_N$ is the new cutoff frequency, $F_O$ is the old cutoff frequency, and A is frequency decrease function having a value between zero and one, and filters the energy envelope using the new cutoff frequency (940). Steps 930 and 940 are then performed in loop until the percentage of "heartbeat" peaks relative to total peaks falls below the threshold percentage.

Once the percentage of "heartbeat" peaks relative to total peaks falls below the threshold percentage, adaptive filter 260 next determines a percentage of wanted peaks in the energy envelope that are not attributable to heart sound and have disappeared as a result of the downward adjustments in the cutoff frequency (950). If the percentage of these wanted non-"heartbeat" peaks is above a threshold percentage, it is presumed that meaningful respiration sound has been lost through filtering and adaptive filter 260 increases the high bound cutoff frequency according to the formula $$F_N = (1+B)F_O$$

where $F_N$ is the new cutoff frequency, $F_O$ is the old cutoff frequency, and B is frequency increase function having a value between zero and one, and filters the energy envelope using the new cutoff frequency (960). Steps 950 and 960 are performed in loop until the percentage of wanted non-"heartbeat" peaks that have disappeared falls below the threshold percentage, at which point the cutoff frequency is considered optimized.

Figure 10:
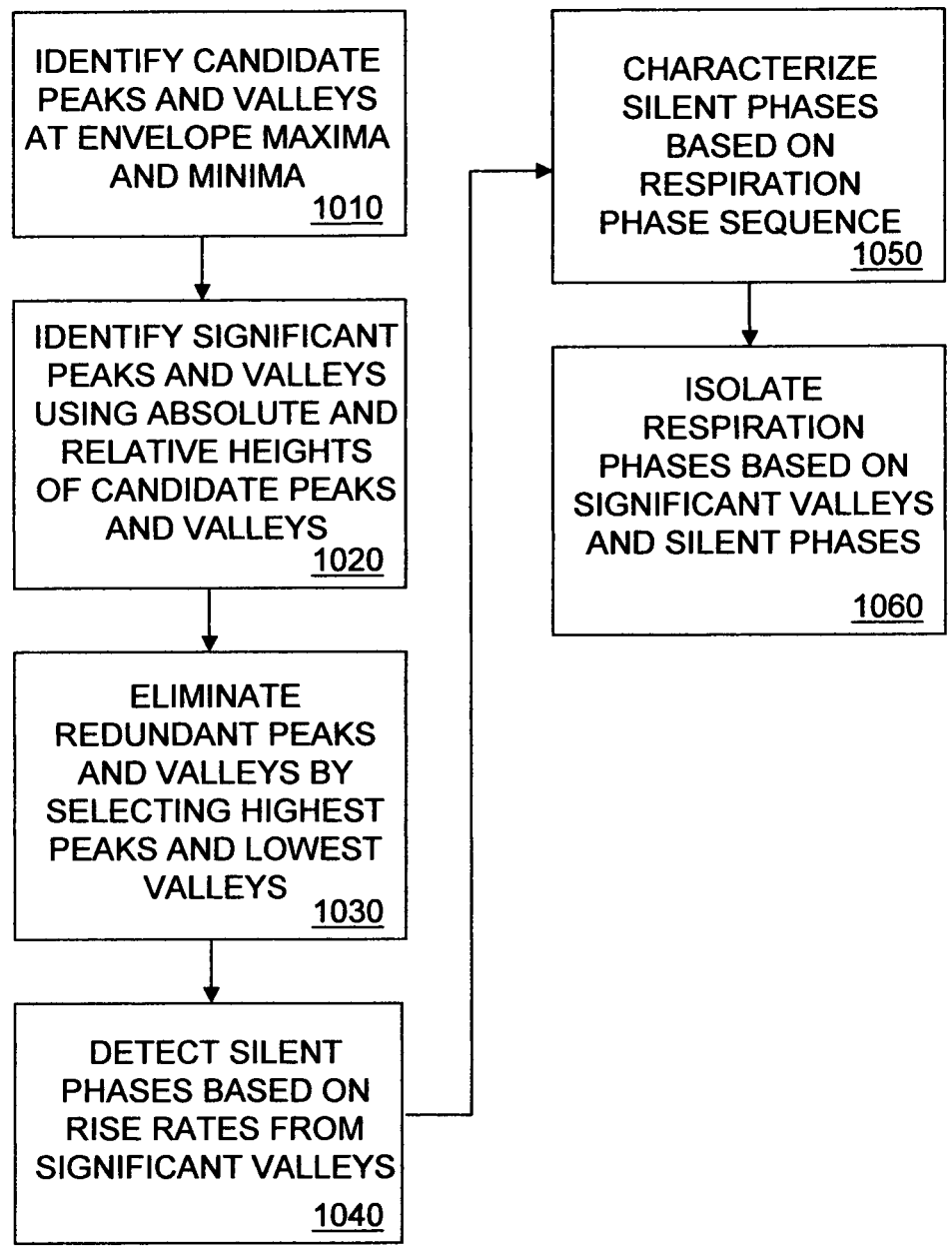
FIG. 10 shows a method for isolating respiration phases in a signal energy envelope in some embodiments of the invention.
Figure 14:
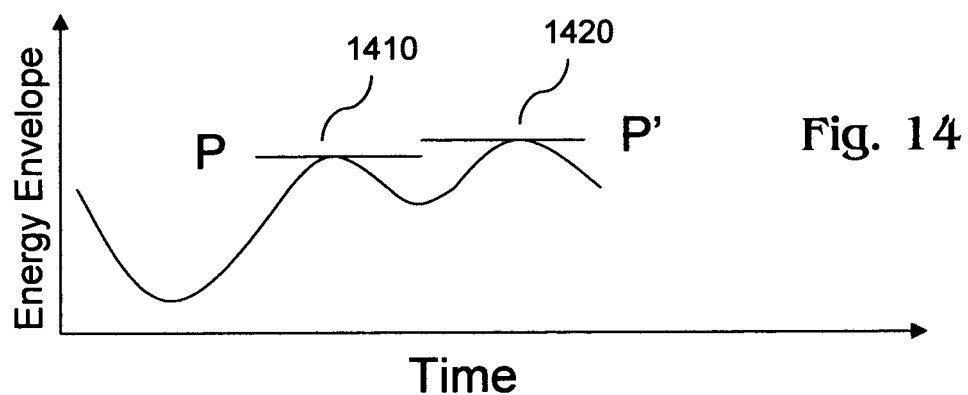
FIG. 14 shows use of signal heights of consecutive significant peaks that are uninterrupted by a significant valley to eliminate a redundant peak in some embodiments of the invention.
Figure 15:
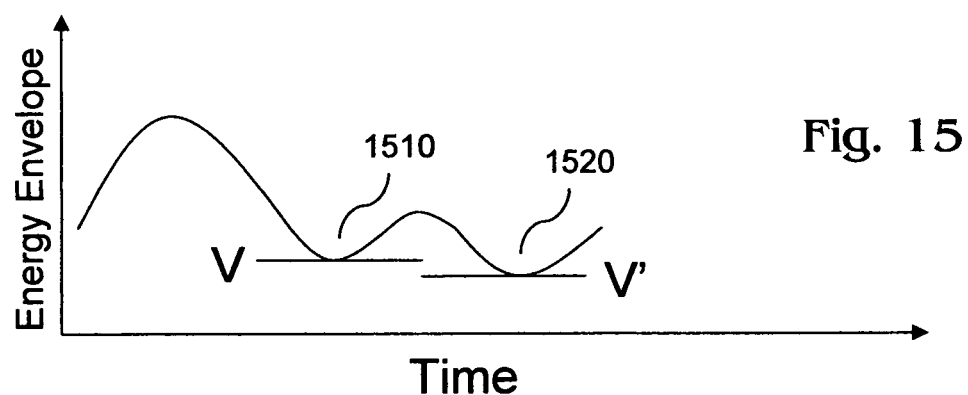
FIG. 15 shows use of signal heights of consecutive significant valleys that are uninterrupted by a significant peak to eliminate a redundant valley in some embodiments of the invention.

Next, respiration phase detector 270 isolates respiration phases in the energy envelope. FIG. 10 shows a method for isolating respiration phases in some embodiments of the invention and will be described in conjunction with FIGS. 11-15. First, phase detector 270 identifies candidate peaks and valleys at maxima and minima of the energy envelope (1010). Phase detector 270 marks all times when the energy envelope reaches a maximum, as indicated by the slope (derivative) falling from a positive value to zero, as candidate peaks. Similarly, phase detector 270 marks all times when the energy envelope reaches a minimum, as indicated by the slope (derivative) rising from a negative value to zero, as candidate valleys. For example, in FIG. 11, an energy envelope is shown to have a first candidate valley 1110, followed by a first candidate peak 1120, followed by a second candidate valley 1130, followed by a second candidate peak 1140.

Next, phase detector 270 selects significant peaks and valleys from among the candidate peaks and valleys using absolute and relative heights of the candidate peaks and valleys (1020). Significant peak and valley selection may be better understood by reference to FIG. 12. There, an energy envelope is shown to have a candidate peak 1220 followed by a candidate valley 1230. Phase detector 270 performs a first check to verify that the absolute height (H1) of candidate peak 1220, that is, the amount by which candidate peak 1220 is above zero, exceeds a minimum absolute height threshold. Phase detector 270 performs a second check to verify that the relative height (H2) of candidate peak 1220, that is, the amount by which candidate peak 1220 is above the immediately preceding significant valley 1210, exceeds a minimum relative height threshold. If candidate peak 1220 passes both checks, phase detector 270 selects candidate peak 1220 as significant; otherwise, phase detector 270 disregards candidate peak 1220. Next, phase detector 270 performs a first check to verify that the absolute height (H3) of candidate valley 1230, that is, the amount by which candidate valley 1230 is above zero, does not exceed a maximum absolute height threshold. Phase detector 270 performs a second check to verify that the relative height (H4) of candidate valley 1230, that is, the amount by which candidate valley 1230 is below the immediately preceding significant peak 1220, exceeds a minimum relative height threshold. If candidate valley 1230 passes both checks, phase detector 270 selects candidate valley 1230 as significant; otherwise, phase detector 270 disregards candidate valley 1230.

Next, phase detector 270 eliminates redundant peaks and valleys by selecting the highest peaks and lowest valleys (1030). Due to background noise, heart sound artifacts or other factors causing signal distortion, the selection of Step 1020 may yield two or more significant peaks that are uninterrupted by a significant valley, and/or may yield two or more significant valleys that are uninterrupted by a significant peak. For example, in FIG. 14, a first significant peak 1410 is followed by a second significant peak 1420 without a significant valley separating peaks 1410, 1420. Accordingly, phase detector 270 disregards the lower significant peak 1410 among the two significant peaks 1410, 1420 as being redundant. Similarly, in FIG. 15, a first significant valley 1510 is followed by a second significant valley 1520 without a significant peak separating valleys 1510, 1520. Accordingly, phase detector 270 disregards the higher significant valley 1510 among the two significant valleys 1510, 1520 as being redundant.

Next, phase detector 270 detects silent phases based on rise rates from significant valleys (1040). In this regard, the respiration phase sequence for certain humans exhibits silent phases, which can be true silent phases attributable to the lack of meaningful airflow or silent expiration phases attributable to expiration not being sufficiently loud to be detected. These silent phases are accounted for in order to reliably isolate respiration phases and reliably estimate respiration parameters. More particularly, the rise rate from each significant valley is determined and a silent phase is identified where the rise rate is below a rise rate threshold after minimum period. In FIG. 13, for example, a significant valley 1310 is followed by a significant peak 1320. Phase detector 270 begins measuring the rise rate from significant valley 1310 after a minimum period $T_{min}$ and determines that the rise rate does not exceed the rise rate threshold until after a period T, at which point the rise rate is characterized by (H6–H5)/T. Accordingly, phase detector 270 designates the period T as a silent phase.

Next, phase detector 270 characterizes silent phases as true silent phases or silent expiration phases based on a respiration phase sequence exhibited by the envelope (1050). For example, if a silent phase detected in the energy envelope follows two consecutive non-silent phases, the silent phase is designated a true silent phase. On the other hand, if a silent phase detected in the energy envelope follows a non-silent phase that was immediately preceded by a silent phase, the silent phase is designated a silent expiration phase. The length of a silent phase may be used as an additional or alternative criterion in characterizing a silent phase, as true silent phases tend to be of shorter duration than silent expiration phases.

Next, phase detector 270 isolates respiration phases based on significant valleys and silent phases (1060). Each period bounded between consecutive significant valleys without any interrupting silent phase is designated a respiration phase. Each period bounded between the end of a silent phase and the next significant valley is designated a respiration phase. And, naturally, each silent expiration phase is designated a respiration phase. Phase detector 270 then passes the energy envelope with isolated respiration phases to respiration data calculator 280.

Calculator 280 generates estimates of one or more respiration parameters for the subject being monitored using the isolated respiration phases in the energy envelope. Monitored respiration parameters may include, for example, respiration rate, fractional inspiration time and/or I/E ratio. Where the respiration phase sequence does not permit inspiration and expiration phases to be readily distinguished, a known technique, such as requiring the subject to explicitly identify an initial inspiration phase, may be invoked to enable inspiration and expiration phases to be differentiated. Calculator 280 transmits the respiration parameter estimates to output system 130 for outputting.

Figure 16:
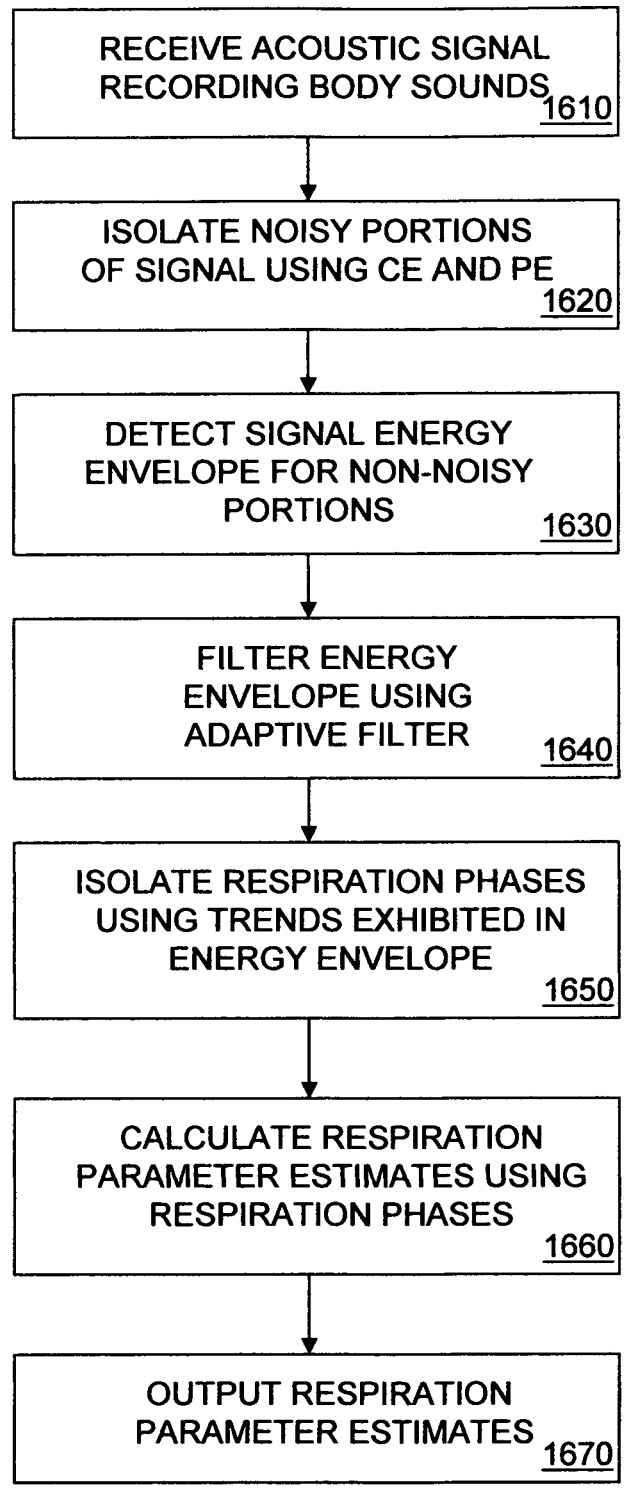
FIG. 16 shows multistage method for estimating one or more respiration parameters from an acoustic signal in some embodiments of the invention.

FIG. 16 shows multistage method for estimating one or more respiration parameters from an acoustic signal in some embodiments of the invention. The method is performed by processing system 120 executing software instructions, in suitable custom logic, or some combination. Processing system 120 receives from sound capture system 110 an acoustic signal recording body sounds (1610). Processing system 120 isolates noisy portions of the signal by analyzing cumulative energies and peak energies in the signal (1620). Processing system 120 detects a signal energy envelope for non-noisy portions of the signal (1630). Processing system 120 filters the energy envelope using an adaptive filter (1640). Processing system 120 isolates respiration phases in the energy envelope using trends exhibited in the energy envelope (1650). Processing system 120 estimates one or more respiration parameters using the isolated respiration phases (1660). Finally, processing system 120 outputs the respiration parameter estimates (1670) to output system 130, which then outputs information based at least in part on the respiration parameter estimates.

It will be appreciated by those of ordinary skill in the art that the invention can be embodied in other specific forms without departing from the spirit or essential character hereof. The present description is thus considered in all respects to be illustrative and not restrictive. The scope of the invention is indicated by the appended claims, and all changes that come with in the meaning and range of equivalents thereof are intended to be embraced therein.

What is claimed is:

1. A method for processing an acoustic signal, comprising the steps of:
    acquiring an acoustic signal recording body sounds on a respiration monitoring system;
    isolating noisy portions of the signal based at least in part on cumulative energies and peak energies in the signal with the system, including detecting first noisy portions of the signal based at least in part on cumulative energies in the signal, detecting second noisy portions of the signal based at least part on peak energies in the signal, designating, as third noisy portions, intersections between first noisy portions that envelop second noisy portions and second noisy portions that are enveloped by first noisy portions, and isolating the third noisy portions;
    detecting an energy envelope for non-noisy portions of the signal with the system;
    filtering the energy envelope using an adaptive filter with the system;
    isolating respiration phases in the energy envelope at least in part by identifying trends in the energy envelope with the system;
    estimating a respiration parameter based at least in part on the respiration phases with the system; and
    outputting information based at least in part on the respiration parameter estimate on the system.

2. The method of claim 1, wherein the first isolating step further comprises designating, as third noisy portions, unions of first noisy portions that do not envelop second noisy portions and second noisy portions that are not enveloped by first noisy portions.

3. The method of claim 1, wherein the filtering step comprises the substeps of identifying unwanted peaks in the energy envelope that are attributable to heart sound; decreasing a high cutoff frequency in response to identifying the unwanted peaks; and applying the decreased high cutoff frequency to the energy envelope.

4. The method of claim 3, wherein the filtering step further comprises the substeps of identifying wanted peaks that were removed from the energy envelope in response to applying the decreased high cutoff frequency; and increasing the high cutoff frequency in response to identifying the wanted peaks.

5. The method of claim 1, wherein the second isolating step comprises the substeps of identifying candidate peaks at maxima of the energy envelope; identifying candidate valleys at minima of the energy envelope; selecting significant peaks from among the candidate peaks using heights of the candidate peaks; selecting significant valleys from among the candidate valleys using heights of the candidate valleys; detecting silent phases in the energy envelope based at least in part on rise rates from the significant valleys; and isolating the respiration phases based at least in part on the significant valleys and the silent phases.

6. The method of claim 5, wherein the isolating substep comprises identifying a true silent phase among the silent phases based at least in part on a respiration phase sequence exhibited by the energy envelope.

7. The method of claim 5, wherein the isolating substep comprises identifying a silent expiration phase among the silent phases based at least in part on a respiration phase sequence exhibited by the energy envelope.

8. The method of claim 1 wherein the respiratory monitoring system is a portable ambulatory monitoring device.

9. A respiration monitoring system, comprising:
a sound capture system adapted to acquire an acoustic signal recording body sounds;
an acoustic signal processing system adapted to receive from the sound capture system the signal, isolate noisy portions of the signal based at least in part on cumulative energies and peak energies in the signal including detecting first noisy portions of the signal based at least in part on cumulative energies in the signal, detecting second noisy portions of the signal based at least part on peak energies in the signal, designating, as third noisy portions, intersections between first noisy portions that envelop second noisy portions and second noisy portions that are enveloped by first noisy portions, and isolating the third noisy portions, detect an energy envelope for non-noisy portions of the signal, filter the energy envelope using an adaptive filter, isolate respiration phases in the energy envelope at least in part by identifying trends in the energy envelope and estimate a respiration parameter based at least in part on the respiration phases; and
a respiration data output system adapted to output information based at least in part on the respiration parameter estimate.

10. The monitoring system of claim 9, wherein the processing system is adapted to designate, as third noisy portions, unions of first noisy portions that do not envelop second noisy portions and second noisy portions that are not enveloped by first noisy portions.

11. The monitoring system of claim 9, wherein the processing system is adapted to identify unwanted peaks in the energy envelope that are attributable to heart sound, is adapted to decrease a high cutoff frequency in response to identifying the unwanted peaks, and is adapted to apply the decreased high cutoff frequency to the energy envelope.

12. The monitoring system of claim 11, wherein the processing system is further adapted to identify wanted peaks that were removed from the energy envelope in response to applying the decreased high cutoff frequency, and is adapted to increase the high cutoff frequency in response to identifying the wanted peaks.

13. The monitoring system of claim 9, wherein the processing system is adapted to identify candidate peaks at maxima of the energy envelope, identify candidate valleys at minima of the energy envelope, select significant peaks from among the candidate peaks using heights of the candidate peaks, select significant valleys from among the candidate valleys using heights of the candidate valleys, detect silent phases in the energy envelope based at least in part on rise rates from the significant valleys, and isolate the respiration phases based at least in part on the significant valleys and the silent phases.

14. The monitoring system of claim 13, wherein the processing system is adapted to identify a true silent phase among the silent phases based at least in part on a respiration phase sequence exhibited by the energy envelope.

15. The monitoring system of claim 13, wherein the processing system is adapted to identify a silent expiration phase among the silent phases based at least in part on a respiration phase sequence exhibited by the energy envelope.

16. The respiratory monitoring system of claim 9, wherein the monitoring system is a portable ambulatory monitoring device.

17. A method for processing an acoustic signal, comprising the steps of:
acquiring an acoustic signal recording body sounds on a respiration monitoring system;
isolating noisy portions of the signal based at least in part on cumulative energies and peak energies in the signal with the system, including detecting first noisy portions of the signal based at least in part on cumulative energies in the signal, detecting second noisy portions of the signal based at least part on peak energies in the signal, designating, as third noisy portions, unions of first noisy portions that do not envelop second noisy portions and second noisy portions that are not enveloped by first noisy portions, and isolating the third noisy portions;
detecting an energy envelope for non-noisy portions of the signal with the system;
filtering the energy envelope using an adaptive filter with the system;
isolating respiration phases in the energy envelope at least in part by identifying trends in the energy envelope with the system;
estimating a respiration parameter based at least in part on the respiration phases with the system; and
outputting information based at least in part on the respiration parameter estimate on the system.

18. A respiration monitoring system, comprising:
a sound capture system adapted to acquire an acoustic signal recording body sounds;
an acoustic signal processing system adapted to receive from the sound capture system the signal, isolate noisy portions of the signal based at least in part on cumulative energies and peak energies in the signal including detecting first noisy portions of the signal based at least in part on cumulative energies in the signal, detecting second noisy portions of the signal based at least part on peak energies in the signal, designating, as third noisy portions, unions of first noisy portions that do not envelop second noisy portions and second noisy portions that are not enveloped by first noisy portions, and isolating the third noisy portions, detect an energy envelope for non-noisy portions of the signal, filter the energy envelope using an adaptive filter, isolate respiration phases in the energy envelope at least in part by identifying trends in the energy envelope and estimate a respiration parameter based at least in part on the respiration phases; and a respiration data output system adapted to output information based at least in part on the respiration parameter estimate.

* * * * *